US00PP25538P3

(12) United States Plant Patent
Yencho et al.

(10) Patent No.: US PP25,538 P3
(45) Date of Patent: May 12, 2015

(54) INDUSTRIAL SWEETPOTATO PLANT NAMED 'NCPUR06-020'

(50) Latin Name: ***Ipomoea batatas* (L.) Lam.**
Varietal Denomination: NCPUR06-020

(71) Applicant: North Carolina State University, Raleigh, NC (US)

(72) Inventors: George Craig Yencho, Raleigh, NC (US); Kenneth Vincent Pecota, Raleigh, NC (US); Jarred Edward Driscoll, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 56 days.

(21) Appl. No.: 13/986,824

(22) Filed: Jun. 7, 2013

(65) Prior Publication Data

US 2014/0366234 P1 Dec. 11, 2014

(51) Int. Cl.
*A01H 5/00* (2006.01)

(52) U.S. Cl.
USPC ..... Plt./258

(58) Field of Classification Search
CPC ..... A01H 5/06
USPC ..... Plt./258
See application file for complete search history.

(56) References Cited

PUBLICATIONS

Yencho, "A vision for the next generation sweetpotato improvement in Africa", Jun. 3-5, 2013 (retrieved from Google Search on Sep. 25, 2014).*

* cited by examiner

*Primary Examiner* — Susan McCormick Ewoldt
*Assistant Examiner* — Keith Robinson
(74) *Attorney, Agent, or Firm* — Myers Bigel Sibley & Sajovec, PA

(57) ABSTRACT

'NCPUR06-020' is a purple-fleshed sweetpotato with high levels of anthocyanin pigments in its storage roots. 'NCPUR06-020' was developed using conventional crossing and breeding methods, and it is intended for use in the natural colorant industry. The anthocyanins present in sweetpotatoes have a number of beneficial properties and they can be used for a wide range of purposes in the food processing and functional food industries.

3 Drawing Sheets

Latin name of the genus and species: The Latin name of the novel plant variety disclosed herein is *Ipomoea batatas* (L.) Lam.

Variety denomination: The inventive variety of *Ipomoea batatas* disclosed herein has been given the varietal denomination 'NCPUR06-020'.

BACKGROUND OF THE INVENTION

'NCPUR06-020' is a purple-fleshed sweetpotato with high levels of anthocyanin pigments in its storage roots. 'NCPUR06-020' was developed using conventional crossing and breeding methods. It is the first purple-fleshed variety in our industrial-type breeding populations to be released and it is intended for use in the natural colorant industry. Most colorants are synthetic and obtained from a wide variety of organic and inorganic sources. Natural and synthetic coloring additives are widely used in the food, cosmetic and pharmaceutical industries to enhance the appearance of products. There has been a recent trend to replace the use of synthetic colorants in food products with natural food colorants that have beneficial health properties and the natural colorant sector is increasing globally. The storage roots of purple-fleshed sweetpotatoes produce several purplish red anthocyanins in large quantities. Anthocyanins are an attractive source of natural colorants because they also possess many beneficial human health properties including antioxidative radicalscavanging abilities, anti-mutagenic, anti-hypertensive, anti-hyperglycemic and hepatoprotective properties.

Using conventional breeding techniques and a diverse array of germplasm, the sweetpotato breeding program developed a population of high pigment value, purple-fleshed sweetpotatoes. These varieties are suitable for anthocyanin extraction, and they are better than the current lines available in the US as they have increased color yields and better disease resistance compared to the existing purple-fleshed sweetpotatoes in the US.

'NCPUR06-020' is the first purple-fleshed sweetpotato variety to be released by the North Carolina State University sweetpotato breeding program. Several purple-fleshed sweetpotato varieties are currently grown and subjected to extraction in Japan and China. As with many other sweetpotato products, China is the largest producer of purple-fleshed sweetpotatoes. We believe there is a significant market for a "Made in the USA" purple-fleshed sweetpotato derived colorant and expect the 'NCPUR06-020' variety to be the first in a series of new purple-fleshed sweetpotatoes to be developed and released by NC State University sweetpotato breeding program for the natural colorant and functional foods sectors.

Lineage. The *Ipomoea batatas* 'NCPUR06-020' variety originated from a conventional cross between *Ipomoea batatas* breeding lines BM85-42 (the female parent; not patented) and NC414 (the male parent; patented as 'Stokes Purple' (U.S. Plant Pat. No. 17,976)). Botanical seed was harvested from this and other purple sweetpotato lines planted in our winter greenhouse-crossing block between September of 2005 and February of 2006. The breeding line BM85-42 is a white-fleshed biomass line from the USDA Vegetable Lab sweetpotato breeding program. The breeding line NC414 was a line provided to the program by a local farmer, which was subsequently patented and named 'Stokes Purple' (Sizemore et al. 2007). Botanical seed from the BM85-42×NC414 cross were planted in a greenhouse located in Raleigh, N.C. on Feb. 8, 2006. Seedlings with storage roots were cut and evaluated for flesh color with purple-fleshed selections being planted in Clinton, N.C. on May 9, 2006 to increase for multiple plant cuttings. Five plant cuttings were taken Jul. 5, 2006 and planted in Kinston, N.C. on Jul. 6, 2006. The variety 'NCPUR06-020' was selected from a five hill plot Oct. 23, 2006 because of its combination of exceptional features. 'NCPUR06-020' was increased, evaluated, and advanced as the variety 'NCPUR06-020', with "06" referring to the year in which it was selected, and "020" indicating that this was the 20th purple selection made by the breeding program in 2006. It has been propagated asexually since this time.

Asexual Reproduction. Since its selection, *Ipomoea batatas* 'NCPUR06-020' has been asexually reproduced at by vegetative propagation of vine cuttings and/or cuttings from root sprouts. Vegetative propagation was done in Clinton N.C. for increase and field evaluation and tissue culture micropropagation and tissue culture propagation was done in Raleigh, N.C. Successively, there have been six cycles of vegetative propagation, one cycle of tissue culture micropropagation, and multiple vegetative propagation cycles to increase the plant population.

Asexual reproduction of 'NCPUR06-020' using these methods has shown that the unique features of the new variety are stable and the plant reproduces true to type in successive generations of asexual reproduction.

SUMMARY OF THE INVENTION

*Ipomoea batatas* 'NCPUR06-020' is a purple-fleshed sweetpotato with high levels of anthocyanin pigments in its storage roots. 'NCPUR06-020' was developed using conventional crossing and breeding methods, and it is intended for use in the natural colorant industry. The anthocyanins present in sweetpotatoes have a number of beneficial properties and can be used for a wide range of purposes in the food processing and functional food industries.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

The following is a detailed description of the botanical characteristics of the new and distinct variety of *Ipomoea batatas* plant known by the denomination 'NCPUR-06-020'. All colors cited herein refer to The Royal Horticultural Society Colour Chart (The Royal Horticultural Society, London, 1995, 4th edition) designations except where general terms of ordinary dictionary significance are used. Botanical descriptors are based on those described by the International Potato Center (CIP), Asian Vegetable Research & Development Center (AVRDC), and International Board for Plant Genetic Resources (IBPGR) in Descriptors of Sweetpotato, Huaman, Z., ed., IBPGR, Rome, Italy (1991), ISBN 92-9043-204-7. Where specific dimensions, sizes, colors, and other characteristics are given, it is to be understood that such characteristics are approximations or averages set forth as accurately as practicable.

TECHNICAL DESCRIPTION OF THE VARIETY

Figure 1:
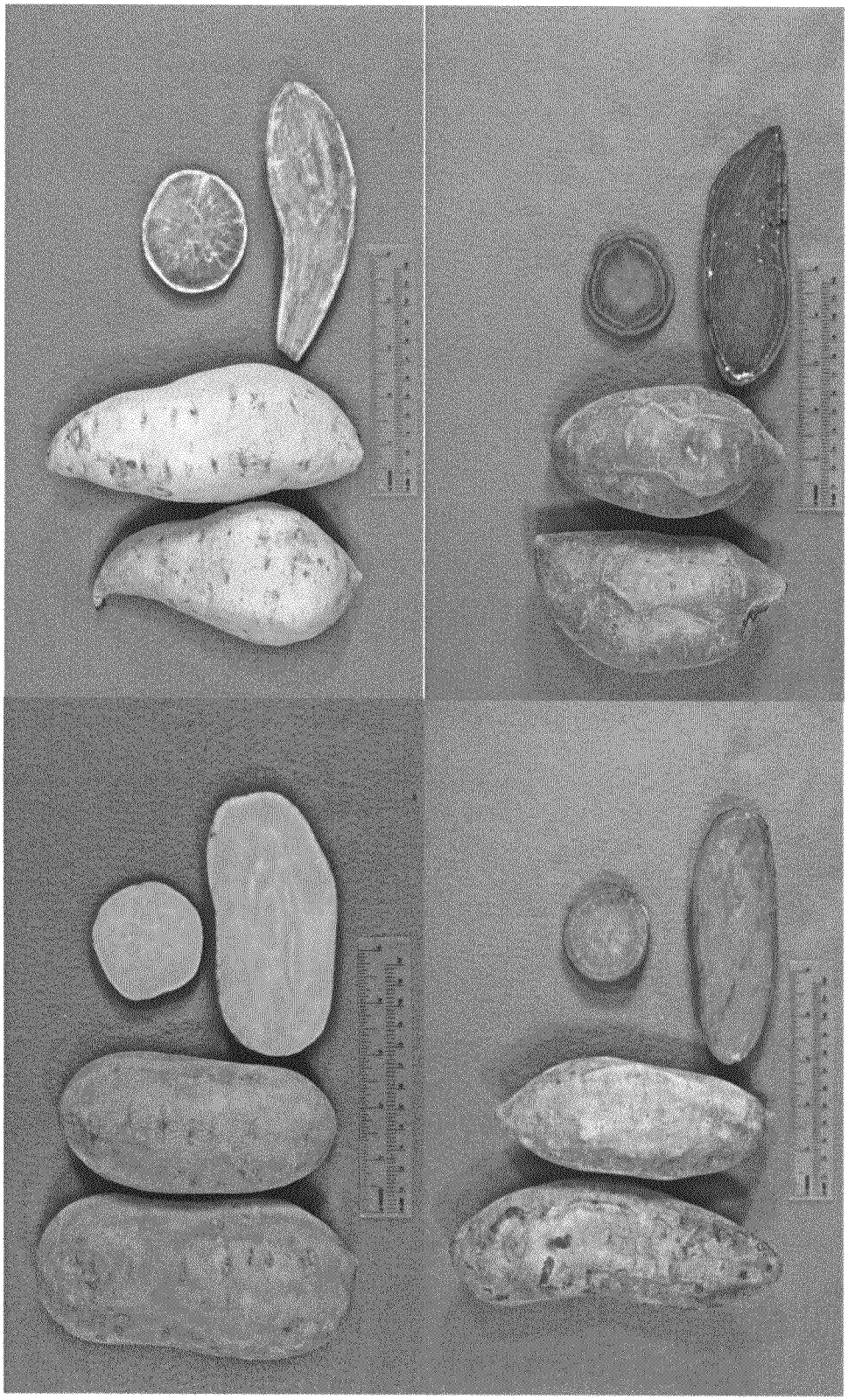
FIG. 1 is a color photograph of representative storage roots of 'Covington' (U.S. Plant Pat. No. 18,516) (upper left), 'Okinawa' (not patented) (upper right), 'Stokes Purple' (lower left) and 'NCPUR-06-020' (lower right).

Storage root characteristics and comparison with other *Ipomoea batatas* varieties: The storage root descriptions provided below are for sweetpotatoes harvested 149 days after planting, then cured for 1 week at 85 F., then stored at 58 F. for seven months. The storage roots of 'NCPUR06-020' are round-elliptic to blocky in shape and dark purple-fleshed (RHS Violet Group N83A to N86A) and they have a dark purple skin color (RHS Greyed Purple Group N187A to N186B) that is smooth to slightly flaky in texture (Table 2 and FIG. 1). The storage roots of 'NCPUR06-020' are not similar in appearance to 'Covington'; the dominant variety produced in the US, which is an orange-fleshed (RHS Orange Group 28B to 28C), smooth-skinned, rose-colored (RHS Orange-Red Group 33D to 34D to Greyed Orange 170C to 170 D to N170C to N171D), table-stock sweetpotato. Of the purple-fleshed varieties currently produced in the U.S., both 'NCPUR06-020' and 'Stokes Purple' have similar skin colors while 'Okinawa', a variety from Hawaii, has a distinct cream to light brown colored skin (RHS colors not determined). The most desirable attribute of 'NCPUR06-020' is its dark purple flesh color, which is the result of high levels of extractable anthocyanins. 'NCPUR06-020' possesses significantly higher levels of anthocyanins and they occur in different ratios compared to 'Stokes Purple' (Tables 1 and 2, and FIG. 1). In terms of anthocyanin production, 'NCPUR06-020' is one of the highest anthocyanin producers in our breeding populations. The average yield (kg/ha), percent dry matter and pigment content (mg/g dry wt.) and total anthocyanin pigment yield (kg/ha) of 'NCPUR06-020' in 6 yield trials during 2009-2011 were 49,656 kg/ha, 30% dry matter content, 3.83 mg/g dry wt, and 58 kg anthocyanins produced per hectare compared with 43,976 kg/ha yield, 29% dry matter content, and anthocyanin production of 1.46 mg/g dry wt and 19 kg/ha for 'Stokes Purple'. Another important diagnostic trait for sweetpotato is the dry matter content of its storage roots. 'NCPUR06-020' storage roots average 30% dry matter content. 'Stokes Purple' and 'Okinawa' average 29% and 26%, respectively, while the orange-fleshed variety 'Covington' averages 19-20% (Table 1).

Plant characteristics: To describe and compare the plant characteristics of the reference varieties to 'NCPUR06-020' three representative specimens of each variety were planted in six-inch azalea pots in a glasshouse. After rooting, plants were treated with 200 ppm 20-10-20 fertilizer daily. Plant measurements were taken in May 2012 from 55-day-old specimens. 'NCPUR06-020' has not been observed under all possible environmental conditions; therefore, the phenotype may vary under different environmental conditions such as season, temperature, light intensity, day length, cultural conditions, and the like, without any variance in the genotype.

Figure 3:
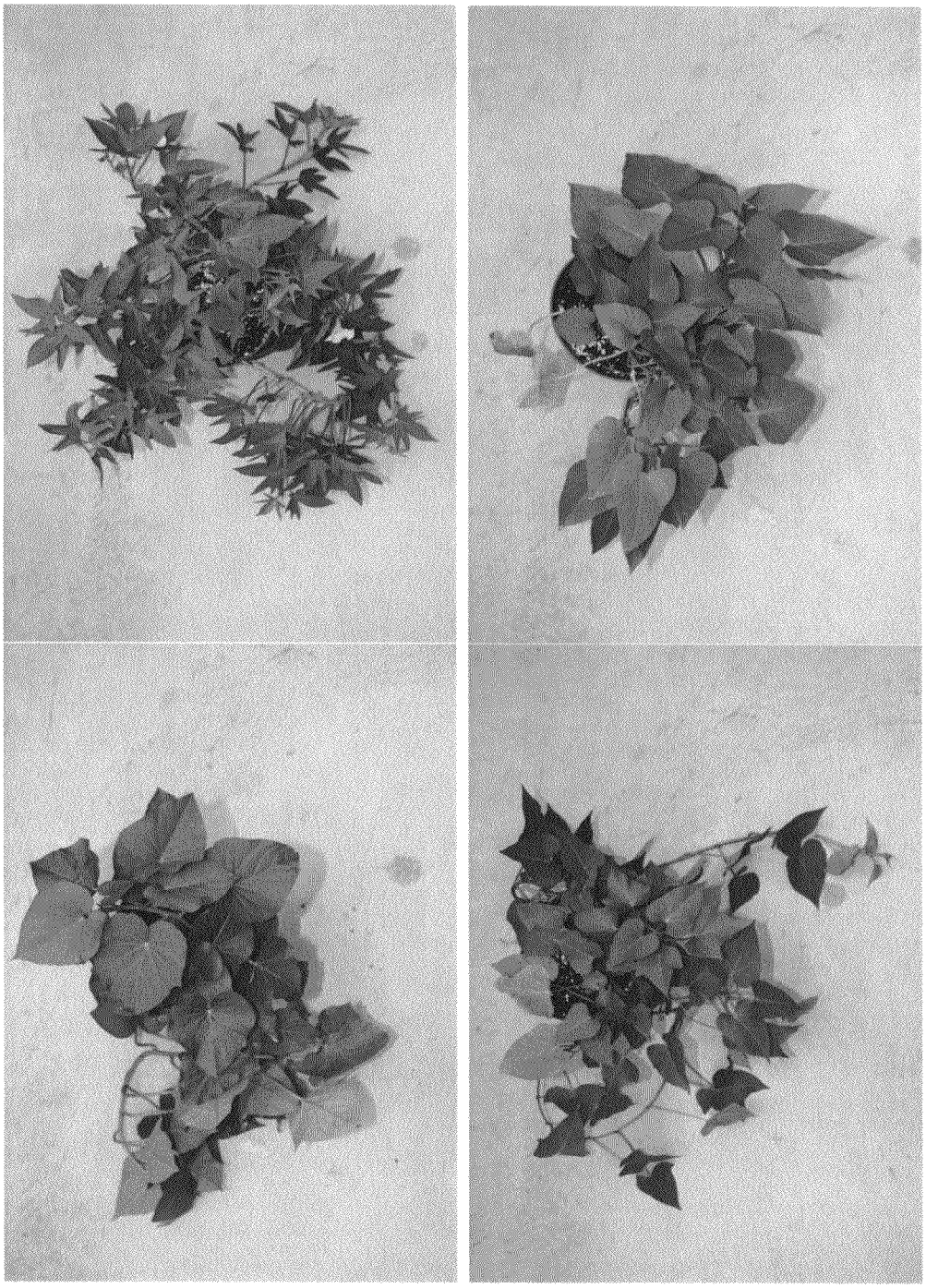
FIG. 3 is a color picture of glasshouse grown 55 day old representative plants of 'Covington' (upper left), 'Okinawa' (upper right), 'Stokes Purple' (lower left) and 'NCPUR-06-020' (lower right).

*Growth conditions.*—'NCPUR06-020' has excellent vigor and a moderate to rapid growth rate (FIG. 3). In locales with mild winter conditions, 'NCPUR06-020' will grow perennially; otherwise it is an annual plant. Similar to other cultivated sweetpotatoes, wind or rain rarely causes much damage to 'NCPUR06-020', but if damage does occur, the plant drops the damaged leaves and grows new shoots at nodes where the leaves were lost. Under low light levels in a greenhouse, 'NCPUR06-020' can develop intumescence, which will remain on the affected foliage, but will be outgrown with new foliage.

*Aboveground structure and coloration.*—FIG. 3 shows the shape and coloration of a typical specimen of 'NCPUR06-020'. Color will vary somewhat due to temperature and nutrient stress. Overall, this variety is a moderately spreading, semi-erect herbaceous plant that has an average height of 15.4 cm and an average area spread of 52.8 cm. The growth habit of this plant is slightly upright with shoots growing outward.

*Branching habit.*—'NCPUR06-020' will produce about 4 lateral branches coming off the stem, averaging about 34.0 cm long with a diameter of about 0.4 cm.

*Vegetative lateral shoots.*—The number of lateral shoots varies, but averages about 6 with several short secondary shoots. Sparse pubescence can be observed on young tips. Lateral branch length: about 14.6 cm. Diameter: about 0.4 cm. Internodes are intermediate with an average length of about 9.8 cm.

*Stem.*—The stems of 'NCPUR06-020' are round and glabrous with an outward, slightly undulating aspect and very strong strength. Color: green (RHS 144A-B) with some purple spots at nodes (RHS 59A).

*Petiole.*—Leaf petiole length varies with an average of about 9.8 cm. Diameter: about 0.25 cm. Color: green (RHS 144A-B) with flush of purple (RHS 59A) at point of attachment to leaf. The surface texture of the petiole is glaborous.

Figure 2:
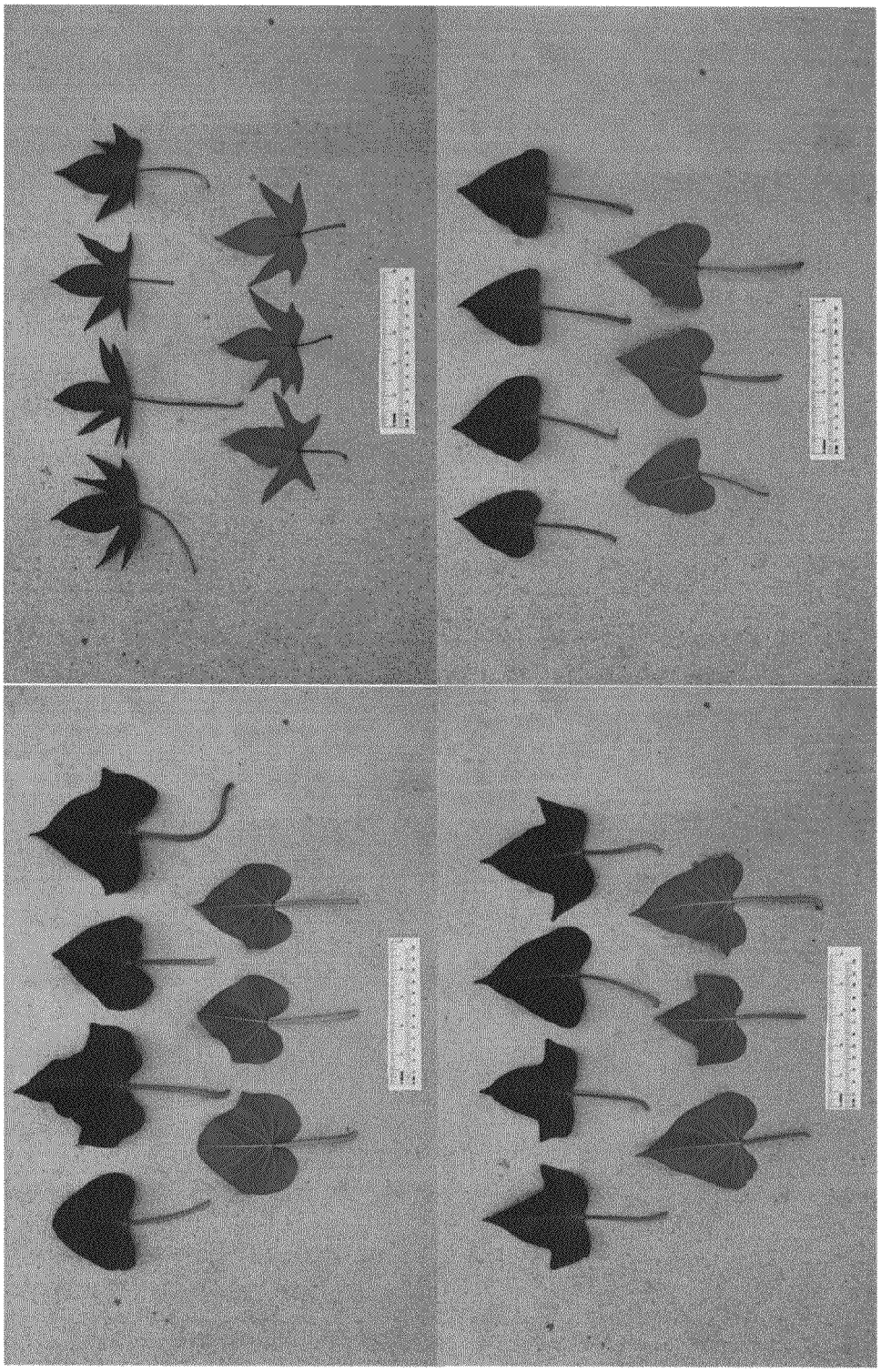
FIG. 2 is a color picture of the abaxial and adaxial surface of representative leaves with petioles attached of 'Covington' (U.S. Plant Pat. No. 18,516) (upper left), 'Okinawa' (not patented) (upper right), 'Stokes Purple' (lower left) and 'NCPUR-06-020' (lower right).

*Foliage.*—Leaves are alternate and tend to slightly spiral around the stem. They are simple and deltoid to cordate with an entire margin. Leaf shape is somewhat variable as is size (see FIG. 2 and FIG. 3). Quantity: Heavily foliated, with about 18 leaves per lateral branch. Mature leaf length: about 11.1 cm. Mature leaf width: about 8.3 cm. The leaf tip is acute. Both the upper and lower surface of the leaf has a glabrous texture and a matte finish with slight pubescence. Both the upper and lower surface of the immature leaves have slight pubescence on the upper surface. Mature leaf color: Green (RHS 137A-B) upper surface, green (RHS 137C) lower surface. Immature leaf color: Green (RHS 137D, 138A) upper surface, green (RHS 138B) lower surface. There is slight purple (RHS 59C) coloration where the leaf meets the petiole (FIG. 2). Venation is pinnate-arcuate. Color: Mature venation color: Green (RHS 144A) upper surface, green (RHS 145B) lower surface with secondary purple (RHS 59B) at petiole junction. Immature venation color: Green (RHS 144B) upper surface, green (RHS 145C) lower surface with secondary purple (RHS 59C) at petiole junction and leaf margin.

*Flowers.*—'NCPUR06-020' flowers sporadically throughout the season in response to a variety of stressful conditions (e.g., drought, nutrient stress, cloudy weather). Flowering is enhanced by short day lengths (<12 hours), but the precise photoperiod for flower induction is currently unknown. The inflorescence is generally a cyme in which there is one solitary peduncle. Peduncles (RHS 143A-B, 59A-B) are green with purple spots at the base, averaging 38.6 mm long from mature leaf axils with an average diameter of 4.1 mm. The surface texture of the peduncle is slightly pubescent. Usually buds of the first and second order are developed, but often, single flowers are produced. Buds (RHS 152D-151D, N77D) are light green with slight light lavender at the tip, and around 27.4 mm in length and 7.7 mm in diameter 24 hours before opening. Bud shape is elliptic to slightly lanceolate. The corolla is composed of five fused petals that form a funnel with a rounded to slightly pentagonal limb. Corolla width: ~49.4 mm, corolla length: ~52.1 mm. The corolla has slight to no fragrance. The limb color is light lavender, while the outer throat color is light lavender and the inner throat color is purple. Inner limb color: RHS 76B-C, Outer limb color: RHS 76A-D, Inner throat color: RHS 77A-B, Outer throat color: RHS 76B-D). There are five sepals, with an average length of 9.4 mm and width of 4.9 mm. The sepals have an obovate to elliptic shape with an obtuse apex and are light green in color with slight purple spots. Outer sepal color: RHS N144A-144A, 59A, Inner sepal color: RHS N144A-144A. Each flower has one pistil with a cream-colored style (RHS 155B). The stigma is cream colored (RHS 155D) and the style averages about 1 mm wide and 18.3 mm long. The stigma is at the same height to slightly inserted relative to the stamens. The ovary is light yellow (RHS 1D) and superior with two locules that contain one or two ovules. At the base of the ovary there are orange basal glands (RHS N163C) containing nectar continuing halfway up the ovary. There are five cream colored anthers (RHS 155B) that are approximately 3.2 mm long. There are five cream fading to purple (RHS 155A, 77B) colored stamens averaging 14.2 mm in length. Pollen (RHS 155B) is moderate. True seed can be obtained via compatible crosses. There is some variation in flower size and color, depending on the environmental conditions.

*Disease resistance or pest resistance/susceptibility.*—'NCPUR06-020' is susceptible to silverleaf whiteflies (*Bemisia tabaci*) and two spotted spidermites (*Tetranychus urticue*) in a greenhouse environment. Based on multiyear disease evaluations using standardized greenhouse and field screening methods as well as field-based observations of the disease reaction of 'NCPUR06-020' to the most important pathogens of sweetpotato in North Carolina, 'NCPUR06-020' is moderately resistant to *Fusarium* wilt (*Fusarium oxysporum* Schlect. *F. sp. batatas* (Wollenw.) Snyd. & Hans.), susceptible to *Streptomyces* soil rot (*Streptomyces ipomoeae* (Person & W. J. Martin) Waksman & Henrici) and moderately susceptible to southern root knot nematode, *Melodogyne incognita* (Kofoid & White).

Plant production characteristics:

The sprout production of 'NCPUR06-020' on plant beds prior to cutting and transplanting in the field is very good with transplant survival in the field being good to excellent.

REFERENCES CITED

Huaman, Z., (ed.). 1991. Descriptors for Sweet Potato. International Potato Center (CIP), Asian Vegetable Research & Development Center (AVRDC), and International Board for Plant Genetic Resources (IBPGR). Rome, Italy. ISBN 92-9043-204-7

Royal Horticultural Society Colour Chart, 4$^{th}$ Ed. 2001. The Royal Horticultural Society, 80 Vincent Square, London, England.

Sizemore, M. E., R. L. Slate, and D. A. Priddy, Jr. 2007. Sweetpotato plant named 'Stokes Purple'. U.S. Plant Pat. No. 17,976 P2, Sep. 4, 2007. 6 pp.

TABLE 1

Average yield, percent dry matter content and anthocyanin production of 'NCPUR06-020' and 'Stokes Purple' in six yield trials conducted during 2009-2011 in NC.

| Variety | Total yield* (kg/ha) | Percent dry matter | Anthocyanin content* (mg/g dry wt) | Anthocyanin yield* (kg/ha) |
|---|---|---|---|---|
| 'NCPUR06-020' | 49,656 | 30 | 3.83 | 58 |
| 'Stokes Purple' | 43,976 | 29 | 1.46 | 19 |

*Differences between total yield, anthocyanin content and anthocyanin yield are highly significant by ANOVA at p = 0.05

TABLE 2

Characteristics of 'NCPUR06-020' compared to the purple-fleshed sweetpotato varieties 'Stokes Purple' and 'Okinawa', and the orange-fleshed variety 'Covington'.

| Characteristic | 'NCPU106-020' | 'Stokes Purple' | 'Okinawa' | 'Covington' |
|---|---|---|---|---|
| Skin color | dark purple (RHS N83A to N86A | dark purple (RHS N80A to N81B) | white to light tan | light to medium rose (RHS 33D to 34D) |

TABLE 2-continued

Characteristics of 'NCPUR06-020' compared to the purple-fleshed sweetpotato varieties 'Stokes Purple' and 'Okinawa', and the orange-fleshed variety 'Covington'.

| Characteristic | 'NCPU106-020' | 'Stokes Purple' | 'Okinawa' | 'Covington' |
|---|---|---|---|---|
| Skin texture | moderately flaky | moderately flaky | moderately smooth | smooth-skinned |
| Flesh color | dark purple, avg intensity 3.5 (RHS N83A to N86A) | purple, avg intensity 2.7 (RHS N80A to N81B) | purple/ cream | orange-fleshed (RHS 28B to 28C), |
| Flesh uniformity | uniform | uniform | not uniform | uniform |
| Yield (low, moderate, high) | moderate | moderate | very low | high |
| Dry matter data | 30% | 29% | 26% | 20% |
| Pest/disease resistance: | | | | |
| Fusarium wilt | moderately resistant | moderately resistant | susceptible | resistant |
| Streptomyces soil | susceptible | susceptible | susceptible | resistant rot |
| Southern root knot nematodes | moderately susceptible | resistant | susceptible | resistant |
| Maturity | late | late | late | medium |
| Root shapes | round-elliptic to blocky | long-elliptic to blocky | fusiform, irregular | blocky |
| Length/diameter ratio | 2.5 | 3.4 | NA | 2.5 |
| Sprout production | very good | very good | poor | good |
| Type of vine/ plant canopy (dense, etc) | dense | dense | moderate | dense |
| Transplant survival (poor, good, excellent?) | very good | very good | good | very good |
| Storability (poor, good, etc) | good | good | fair | very good |
| Consumer Quality (backing quality, flavor) | bitter, not palatable | good to fair | good to fair | very good |
| Average Anthocyanin content (mg/g dry wt) | 3.8 | 1.6 | NA | none |
| Average % Peonidin: Cyanidin Ratio | 20%:80% | 78%:12% | NA | none |

What is claimed is:

1. A new and distinct variety of *Ipomoea batatas* industrial sweetpotato plant named 'NCPUR06-020', substantially as illustrated and described herein.

* * * * *

UNITED STATES PATENT AND TRADEMARK OFFICE

CERTIFICATE OF CORRECTION

PATENT NO. : PP25,538 P3
APPLICATION NO. : 13/986824
DATED : May 12, 2015
INVENTOR(S) : Yencho et al.

It is certified that error appears in the above-identified patent and that said Letters Patent is hereby corrected as shown below:

IN THE SPECIFICATION

Column 8, TABLE 2-continued, Line 22: Please correct:

| | | | | |
|---|---|---|---|---|
| Streptomyces soil | susceptible | susceptible | susceptible | resistant rot |

to read as

| | | | | |
|---|---|---|---|---|
| Streptomyces soil rot | susceptible | susceptible | susceptible | resistant |

Signed and Sealed this
Tenth Day of November, 2015

Michelle K. Lee

Michelle K. Lee
*Director of the United States Patent and Trademark Office*